US010421065B2

(12) United States Patent
Zhang et al.

(10) Patent No.: US 10,421,065 B2
(45) Date of Patent: Sep. 24, 2019

(54) WATER SPLITTING CATALYST CONTAINING MN₄CAO₄ CORE STRUCTURE, PREPARATION PROCESS AND APPLICATION THEREOF

(71) Applicant: INSTITUTE OF CHEMISTRY, CHINESE ACADEMY OF SCIENCES, Beijing (CN)

(72) Inventors: Chunxi Zhang, Beijing (CN); Changhui Chen, Beijing (CN)

(73) Assignee: INSTITUTE OF CHEMISTRY, CHINESE ACADEMY OF SCIENCES, Beijing (CN)

( * ) Notice: Subject to any disclaimer, the term of this patent is extended or adjusted under 35 U.S.C. 154(b) by 142 days.

(21) Appl. No.: 15/549,256

(22) PCT Filed: Feb. 2, 2016

(86) PCT No.: PCT/CN2016/073203
§ 371 (c)(1),
(2) Date: Aug. 7, 2017

(87) PCT Pub. No.: WO2016/124133
PCT Pub. Date: Aug. 11, 2016

(65) Prior Publication Data
US 2018/0008969 A1     Jan. 11, 2018

(30) Foreign Application Priority Data

Feb. 6, 2015   (CN) .......................... 2015 1 0065238

(51) Int. Cl.
*B01J 31/22*        (2006.01)
*C01B 13/02*       (2006.01)
(Continued)

(52) U.S. Cl.
CPC .......... *B01J 31/22* (2013.01); *B01J 31/2239* (2013.01); *C01B 13/02* (2013.01); *C07F 13/005* (2013.01);
(Continued)

(58) Field of Classification Search
None
See application file for complete search history.

(56) References Cited

FOREIGN PATENT DOCUMENTS

| CN | 101134723 A | 3/2008 |
|---|---|---|
| CN | 104761591 A | 7/2015 |
| WO | 2012154436 A2 | 11/2012 |

OTHER PUBLICATIONS

McEvoy et al. Chemical Review, 2006, vol. 106, 4467-4468 (Year: 2006).*

(Continued)

*Primary Examiner* — Yun Qian
(74) *Attorney, Agent, or Firm* — Novick, Kim & Lee, PLLC; Allen Xue

(57) ABSTRACT

The present invention provides a process for preparing a water splitting catalyst containing [Mn₄CaO₄] core structure and use thereof. The present invention provides clusters containing [Mn₄CaO₄] core structure by a chemical synthesis using inexpensive metal ions (Mn²⁺, Ca²⁺ ions), simple carboxyl ligands and a permanganate, performed single crystal X-ray diffraction on their space structure, and characterized their physical and chemical properties with electron spectrum, electrochemical and electron paramagnetic resonance technologies and the like. These compounds can catalyze water splitting in the presence of oxidant to release oxygen and can also catalyze water splitting on the surface of an electrode to release electrons onto the surface of the electrode to form a current.

15 Claims, 4 Drawing Sheets

(51) Int. Cl.
  *C07F 19/00*  (2006.01)
  *C25B 1/04*   (2006.01)
  *C25B 5/00*   (2006.01)
  *C07F 13/00*  (2006.01)

(52) U.S. Cl.
  CPC ............... *C07F 19/00* (2013.01); *C25B 1/04* (2013.01); *C25B 5/00* (2013.01); *B01J 2231/70* (2013.01); *B01J 2531/0205* (2013.01); *B01J 2531/0216* (2013.01); *B01J 2531/22* (2013.01); *B01J 2531/23* (2013.01); *Y02E 60/366* (2013.01)

(56) References Cited

OTHER PUBLICATIONS

Zhang, C. et al. "A synthetic Mn4Ca-cluster mimicking the oxygen-evolving center of photosynthesis." Science, May 8, 2015, pp. 690-693, vol. 348, Issue 6235.

Chen, Changhui et al.: "A synthetic model for the oxygen-evolving complex in Sr2+-containing photosystem II.", Chemical Communications, Apr. 25, 2014, pp. 9263-9265, vol. 50, No. 66.

Kanady, J.S. et al.: "Toward Models for the Full Oxygen-Evolving Complex of Photosystem II by Ligand Coordination to Lower the Symmetry of the Mn3CaO4 Cubane: Demonstration That Electronic Effects Facilitate Binding of a Fifth Metal", J. Am. Chem. Soc., Sep. 20, 2014, pp. 14373-14376, vol. 136, No. 41.

Wang, Ya'Nan et al.: "Assignment of the μ4-O5 atom in catalytic center for water oxidation in photosystem II", Chinese Science Bulletin, Jul. 1, 2013 (Jul. 1, 2013), pp. 2717-2720, vol. 58, No. 26.

Mukherjee, S. et al.: "Synthetic Model of the asymmetric [Mn3CaO4] cubane core of the oxygen-evolving complex of photosystem II", PNAS, Feb. 14, 2012, pp. 2257-2262, vol. 109, No. 7.

Suga, M. et al.: "Native Structure of photosystem II at 1.95 A resolution viewed by femtosecoond X-ray pulses", Nature, Jan. 1, 2015, pp. 99-103, vol. 517, Macmillan Publishers Limited.

Chen, C. et al.: "Artificial synthetic MnIVCa-oxido complexes mimic the oxygen-evolving complex in photosystem II", Dalton Transactions, 2015, pp. 4431-4435, 44.

* cited by examiner

WATER SPLITTING CATALYST CONTAINING MN₄CAO₄ CORE STRUCTURE, PREPARATION PROCESS AND APPLICATION THEREOF

TECHNICAL FIELD

The present invention relates to a novel type of biomimetic water splitting catalysts. In particular, the present invention relates to a water splitting catalyst containing a [Mn₄CaO₄] core structure, preparation process and application thereof. This type of compounds could be used as artificial catalysts for catalyzing water splitting.

BACKGROUND ART

Energy crisis and environmental pollution are two key issues that constrain the sustained development of current human society. Since solar energy is inexhaustible, clean and pollution-free and water is one of the most abundant substances on earth, if the solar energy can be utilized to split water efficiently and safely to release oxygen and obtain electrons and protons, to thereby generate electrical energy or hydrogen energy, the energy crisis and environmental pollution issues that human society faces can thus be solved fundamentally. Furthermore, because water is a thermodynamically very stable chemical substance, it is necessary to provide a suitable water splitting catalyst to achieve efficient and safe water splitting. Recently, an international research team has used ions of Ru, Ir and other metal with some complex ligands to synthesize artificial catalysts having water-splitting function. However, all the reported catalysts do not have high catalytic efficiency in water splitting and need the presence of a strong oxidant (such as $Ce(NH_4)_2(NO_3)_6$) to split water. In addition, these known artificial catalysts, which use either noble metals or complex ligands, could lead to high preparation cost and easily cause environmental pollution and thus cannot be popularized and applied. Therefore, there is still an unsolved scientific problem about how to obtain an efficient, inexpensive and environmentally friendly water splitting catalyst.

The photosystem II of photosynthetic organisms is the only biological system in nature that be able to utilize inexpensive metal ions (Mn, Ca) efficiently and safely to achieve water splitting, obtain electrons and protons, and release oxygen at the same time. The key reason why the photosystem II is able to split water efficiently and safely is that it has a unique Mn₄Ca cluster as the biological water splitting catalyst. Recent high-resolution study of the three-dimensional crystal structure of the photosystem II has found that the biological water splitting catalyst has the core of an asymmetric $[Mn_4CaO_n]$ (n value dependent on the redox state of catalyst, which can be 4 or 5) heteronuclear metal cluster, which is formed by a $O^{2-}$ bridging between a Mn₃CaO₄ cubic alkane and a Mn ion. The biological water splitting catalyst at its periphery are provided with the ligands of six carboxyl groups, one imidazole and four water molecules. During the water splitting process, the biocatalyst undergoes five different states ($S_0$, $S_1$, $S_2$, $S_3$, $S_4$). Among them, the valence states of the four manganese ions in the dark steady state ($S_1$ state) are +3, +3, +4 and +4, respectively. The water splitting biocatalytic center of the photosystem II provided an ideal blueprint for the development of an inexpensive, efficient, and environmentally friendly artificial water splitting catalyst. Currently, how to chemically synthesize and prepare those similar to the biological water splitting catalytic center is an important scientific frontier and also a very challenging scientific problem. In this regard, no successful case has been reported yet.

The present invention hereby provides a novel process by a two-step synthesis using inexpensive metal ions ($Mn^{2+}$, $Ca^{2+}$ ions), a simple organic carboxylic acid and $MnO_4^-$ as starting materials, to give an asymmetric $[Mn_4CaO_n]$ core structure formed by an $O^{2-}$ bridging between a Mn₃CaO₄ cubic alkane and a Mn ion. The peripheral ligands of the [Mn₄CaO₄] consists of eight carboxyl anions and three exchangeable neutral ligands. The valence states of the four manganese ions are +3, +3, +4 and +4, respectively. These compounds have structures very similar to the biological water splitting catalytic center. Furthermore, we have found that these compounds also have physical and chemical properties similar to those of the biological water splitting catalytic center. Such compounds can catalyze the splitting of water to release oxygen in the presence of oxidant and can transfer the electrons released by the splitting of water to the surface of the electrode to form current. This type of compounds and their derivatives obtained by structural modification can be used as artificial catalysts for water splitting.

Contents of the Invention

The invention adopts a simple inorganic compounds of $Mn^{+2}$ or $Ca^{2+}$, a simple organic carboxylic acid and uses permanganate anion as oxidant in a two-step synthesis to obtain a water splitting catalyst containing [Mn₄CaO₄] asymmetric cluster. These novel catalysts can catalyze the splitting of water in the presence of an oxidant to release oxygen. They can also catalyze the splitting of water on electrode surface to release the electrons onto the electrode surface to form a current.

The object of the present invention is to provide a series of a water splitting catalysts containing [Mn₄CaO₄] core structure, preparation method and application thereof.

The invention can be realized by the following technical solutions:

(1) a $[Mn_4CaO_4](R_1CO_2)_8(L_1)(L_2)(L_3)$ compound represented by formula (I), characterized in that the compound comprises four Mn ions and one $Ca^{2+}$ ion, which are linked via four $O^{2-}$ ions to form an asymmetric [Mn₄CaO₄] heteronuclear metal cluster skeleton core.

The peripheral ligands of the [Mn₄CaO₄] cluster are provided with eight carboxylic acid anions ($R^1CO_2^-$) and three neutral ligands ($L_1$, $L_2$, $L_3$). The valence states of the four Mn ions are +3, +3, +4 and +4 respectively, and the whole cluster is electrically neutral;

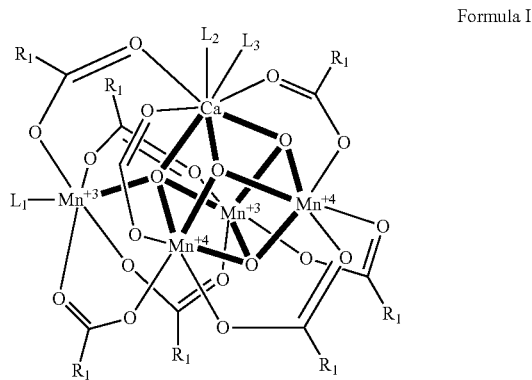

Formula I wherein, $R_1$ is selected from H or $C_{1-8}$ linear or branched alkyl;

the three ligands $L_1$, $L_2$ and $L_3$ are the same or different and are each independently selected from the group consisting of carboxylic acid molecules and derivatives thereof, pyridine, imidazole, pyrazine, quinoline, isoquinoline and derivatives thereof, or water molecule, alcohol molecules, ketones, nitriles (such as acetonitrile), esters and other exchangeable neutral small molecules.

According to a preferred embodiment of the present invention, the carboxylic acid anion ($R_1CO_2^-$) can be carboxylic acid anions such as formic acid, acetic acid, propionic acid, butyric acid, isobutyric acid, valeric acid, isovaleric acid, pivalic acid and hexanoic acid. That is, $R_1$ can be hydrogen (H), methyl (—$CH_3$), ethyl (—$C_2H_5$), n-propyl (—$CH_2CH_2CH_3$), isopropyl (—$CH(CH_3)_2$), n-butyl (—$(CH_2)_3CH_3$), isobutyl (—$CH(CH_3)C_2H_5$), tert-butyl (—$C(CH_3)_3$), n-pentyl (—$(CH_2)_4CH_3$), isopentyl (—$CH(CH_3)C_3H_8$), etc.

Particularly preferred, the compound of formula I is selected from the group consisting of:

[$Mn_4CaO_4(R_1CO_2)_8$]($L_1$)($L_2$)($L_3$), wherein $R_1$=tert-butyl; $L_1$=pyridine; $L_2$=$L_3$=pivalic acid;

[$Mn_4CaO_4(R_1CO_2)_8$]($L_1$)($L_2$)($L_3$), wherein $R_1$=tert-butyl; $L_1$=$L_2$=pyridine; $L_3$=pivalic acid; and

[$Mn_4CaO_4(R_1CO_2)_8$]($L_1$)($L_2$)($L_3$), wherein $R_1$=tert-butyl; $L_1$=isoquinoline, $L_2$=$L_3$=pivalic acid.

Most preferably, the compound is selected from any of the following compounds:

[$Mn_4CaO_4(R_1CO_2)_8$]($L_1$)($L_2$)($L_3$), wherein $R_1$=tert-butyl; $L_1$=pyridine; $L_2$=$L_3$=pivalic acid (2,2-dimethylpropionic acid, or trimethyl acetic acid corresponding to $R_1COOH$, wherein $R_1$ is of tert-butyl structure); its single crystal being monoclinic, space group being $P2_1/c1$, cell parameter being a=29.317(7)Å, b=18.894(4)Å, c=29.903(7)Å, α=90.00°, β=104.609(4)°, γ=90.00°, Z=8, volume being 16028(7)Å$^3$, and its structure being shown by the following formula I-1:

formula I-1

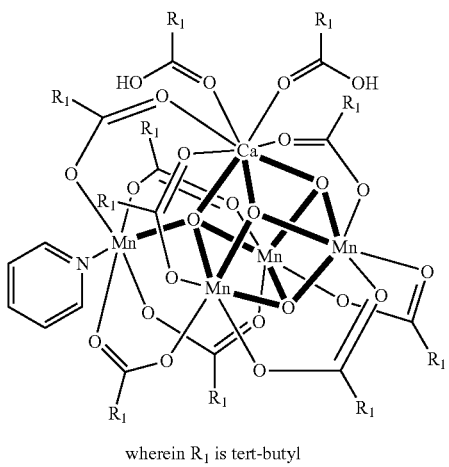

wherein $R_1$ is tert-butyl

[$Mn_4CaO_4(R_1CO_2)_8$]($L_1$)($L_2$)($L_3$), wherein $R_1$=tert-butyl; $L_1$=$L_2$=pyridine; $L_3$=pivalic acid; its single crystal being monoclinic, space group being $P2_1/c1$, cell parameter being a=21.969(4)Å, b=25.326(5)Å, c=29.236(6)Å, α=90.00°, β=102.70(3)°, γ=90.00°, Z=8, volume being 15869(6)Å$^3$; and its structure being shown by the following formula I-2:

formula I-2

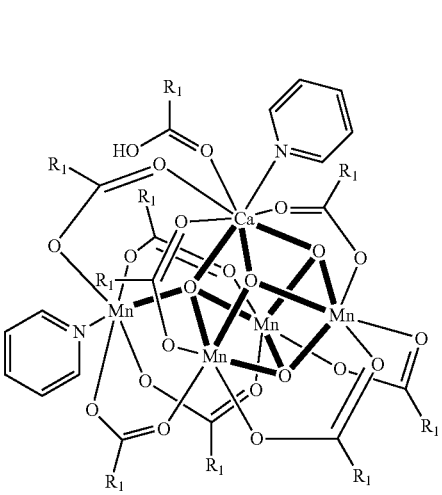

wherein $R_1$ is tert-butyl

[$Mn_4CaO_4(R_1CO_2)_8$]($L_1$)($L_2$)($L_3$), wherein $R_1$=tert-butyl; $L_1$=isoquinoline, $L_2$=$L_3$=pivalic acid; its single crystal being trigonal, space group being R-3, cell parameter being a=38.379(5)Å, b=38.379(5)Å, c=35.682(7)Å, α=90.00°, β=90.00°, γ=120.00°, Z=18, volume being 45517(12)Å$^3$; its structure being shown by the following formula I-3:

formula I-3

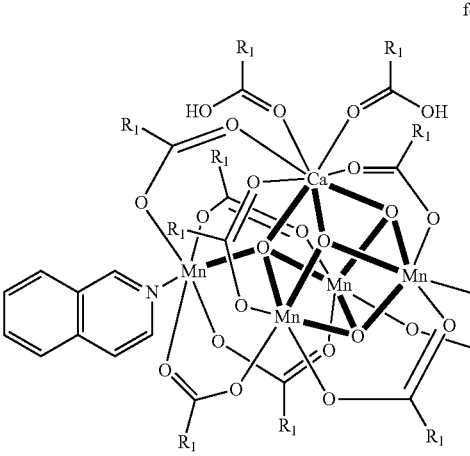

wherein $R_1$ is tert-butyl (2) Process for preparing the compound [$Mn_4CaO_4$]($R_1CO_2$)$_8$($L_1$)($L_2$)($L_3$) represented by formula I, characterized in that the process comprises:

step 1: heating acid (preferably organic carboxylic acid), oxidant, $Mn^{2-}$ and $Ca^{2+}$ salts in a molar ratio of x:y:1:1 (x=10-120; y=1-10, preferably x=20-100, y=2-8) in acetonitrile solution for reacting for 10-60 minutes to obtain a brown solution, filtering to remove precipitate; crystallizing the solution at 0° C. to obtain brown crystals;

step 2: dissolving the brown crystals obtained in step 1 in a ester solvent, and adding organic ligands $L_1$, $L_2$ and $L_3$ to crystallize to obtain the final product.

According to the present invention, the reagents used are as follows: the divalent manganese salt of $Mn^{2+}$ can be selected from various carboxylic acid salts containing $Mn^{2-}$, wherein the carboxylic acid anion ($R_1CO_2^-$) is as described above, such as formate, acetate, propionate, butyrate, isobutyrate, valerate, isovalerate, pivalate, hexanoate and other carboxyl groups as well as derivatives thereof (preferably acetate, pivalate). The divalent manganese salt of $Mn^{2+}$ can also be selected from the divalent manganese salts such as $Mn(ClO_4)_2$, $MnSO_4$, $Mn(NO_3)_2$, and $Mn(CF_3SO_3)_2$. These salts can be their derivatives containing different numbers of crystal water (the number of the crystal water is n=0-6, preferably 1-5 or 2-4).

$Ca^{2+}$ salt can be selected from various carboxylic acid salts of calcium, wherein the carboxylic acid anion ($R_1CO_2^-$) is as described above, such as formate, acetate, propionate, butyrate, isobutyrate, valerate, isovalerate, pivalate, hexanoate and other carboxyl groups as well as derivatives thereof (preferably acetate, pivalate). $Ca^{2+}$ salt can also be selected from the calcium salts such as $Ca(ClO_4)_2$, $Ca(NO_3)_2$, $Ca(CF_3SO_3)_2$. These salts can be their derivatives containing different numbers of crystal water (n=0-6, preferably 1-5 or 2-4).

The oxidant is preferably permanganate anionic oxidant, more preferably tetrabutylammonium permanganate $((C_4H_9)_4NMnO_4)$.

The acid is preferably organic carboxylic acid, such as formic acid, acetic acid, propionic acid, butyric acid, isobutyric acid, valeric acid, isovaleric acid, pivalic acid, hexanoic acid and other carboxyl groups and derivatives thereof (preferably acetic acid, pivalic acid).

The volume of the acetonitrile solvent in step 1 is about 60-100 ml acetonitrile per mmol calcium salt. This reaction can only be carried out in acetonitrile solvent, while the target compound cannot be obtained in either alcohol or other organic solvents.

According to the present invention, the ester organic solvent in the recrystallization of step 2 can be ethyl acetate, methyl acetate, propyl propionate and other esters.

The organic ligands can be the same or different and are each independently selected from the group consisting of carboxylic acid molecules and derivatives thereof, pyridine, imidazole, pyrazine, quinoline and derivatives thereof, or water molecule, alcohol molecules, ketones, nitriles (such as acetonitrile), esters and other exchangeable neutral small molecules.

The reaction temperature is 60° C.-90° C.

The reaction time may be 10-60 minutes.

The present invention further provides the use of the compound of formula I as water splitting catalyst.

Preferably, the compound of formula I of the present invention is used to drive the catalytic splitting of water on the surface of an electrode, or in the presence of an oxidant (which may be a stable oxidant, or a light-induced transient oxidant), to release oxygen, protons and electrons.

The present invention further provides a water splitting catalyst, characterized in that the catalyst comprises an $[Mn_4CaO_4](R_1CO_2)_8(L_1)(L_2)(L_3)$ compound of the present invention as described above.

According to a preferred technical solution of the present invention, the molecular formula of the compound 1 of the present invention is $C_{55}H_{97}CaMn_4NO_{24}$, with the structure of $[Mn_4CaO_4(R_1CO_2)_8](L_1)(L_2)(L_3)$, wherein $R_1$=tert-butyl; $L_1$=pyridine; $L^2=L_3$=pivalic acid. It is monoclinic with space group of $P2_1/c1$, cell parameter of a=29.317(7)Å, b=18.894(4)Å, c=29.903(7)Å, α=90.00°, β=104.609(4)°, γ=90.00°, Z=8, and volume of 16028(7)Å$^3$. The crystal structure is shown in FIG. 1, and the single crystal parameters are shown in Table 1.

TABLE 1 the single crystal parameters of compound 1

| | |
|---|---|
| Molecular formula | $C_{55}H_{97}CaMn_4NO_{24}$ |
| Molecular weight (g/mol) | 1416.18 |
| Temperature (K) | 173.15 |
| Wavelength (Å) | 0.71073 |
| Crystal system | Monoclinic |
| Space group | $P2_1/c1$ |
| Cell parameter | a = 29.317(7)(Å) |
| | b = 18.894(4)(Å) |
| | c = 29.903(7)(Å) |
| | α = 90.00(°) |
| | β = 104.609(4)(°) |
| | γ = 90.00(°) |
| Volume V(Å$^3$) | 16028(7) |
| Number of molecules in one unit cell | 8 |
| Calculated density Dc(g/cm$^3$) | 1.174 |
| Absorption coefficient (mm$^{-1}$) | 0.742 |
| Single crystal size | 0.50 × 0.09 × 0.06 mm |
| F(000) | 5968 |
| θ range | 0.718-27.554°. |
| Collected data number | 65328 |
| Independent data number | 35542 [R(int) = 0.1352] |
| Final R factor [I > 2σ(I)] | $R_1$ = 0.1633 |
| | $wR_2$ = 0.36917 |
| R factor of all data | $R_1$ = 0.2357 |
| | $wR_2$ = 0.4178 |
| Maximum and minimum electron diffraction densities | 1.057 and −0.734e.Å$^{-3}$ |

The molecular formula of the compound 2 of the present invention is $C_{55}H_{92}CaMn_4N_2O_{24}$, with the structure of $[Mn_4CaO_4(R_1CO_2)_8](L_1)(L_2)(L_3)$, wherein $R_1$=tert-butyl; $L_1=L_2$=pyridine; $L_3$=pivalic acid. It is monoclinic with space group of $P2_1/c1$, cell parameter of a=21.969(4)Å, b=25.326(5)Å, c=29.236(6)Å, α=90.00°, β=102.70(3)°, γ=90.00°, Z=8, and volume of 15869(6)Å$^3$. The crystal structure is shown in FIG. 2, and the single crystal parameters are shown in Table 2.

TABLE 2 the single crystal parameters of compound of formula I-2

| | |
|---|---|
| Molecular formula | $C_{55}H_{92}CaMn_4N_2O_{24}$ |
| Molecular weight (g/mol) | 1393.15 |
| Temperature (K) | 173.15 |
| Wavelength (Å) | 0.71073 |
| Crystal system | Monoclinic |
| Space group | $P2_1/c1$ |
| Cell parameter | a = 21.969(4)(Å) |
| | b = 25.326(5)(Å) |
| | c = 29.236(6)(Å) |
| | α = 90.00(°) |
| | β = 102.70(3)(°) |
| | γ = 90.00(°) |
| Volume V(Å$^3$) | 15869(6) |
| Number of molecules in one unit cell | 8 |
| Calculated density Dc(g/cm$^3$) | 1.154 |
| Absorption coefficient (mm$^{-1}$) | 0.746 |
| Single crystal size | 0.21 × 0.15 × 0.09 mm |
| F(000) | 5788 |
| θ range | 0.950-25.200°. |
| Collected data number | 90869 |
| Independent data number | 28547 [R(int) = 0.1329] |
| Final R factor [I > 2σ(I)] | $R_1$ = 0.1696 |
| | $wR_2$ = 0.4033 |
| R factor of all data | $R_1$ = 0.2115 |
| | $wR_2$ = 0.4327 |
| Maximum and minimum electron diffraction densities | 1.441 and −1.607e.Å$^{-3}$ |

The molecular formula of the compound 3 of the present invention is $C_{55}H_{99}CaMn_4NO_{24}$ with structure of $[Mn_4CaO_4(R_1CO_2)_8](L_1)(L_2)(L_3)$, wherein $R_1$=tert-butyl; $L_1$=isoquinoline, L2=L3=pivalic acid. It is trigonal with space group of R-3, cell parameter of a=38.379(4)Å, b=38.379(5)Å, c=35.682(4)Å, α=90.00°, β=90.00°, γ=120.00°, Z=18, and volume of 45517(12)Å$^3$. The crystal structure is shown in FIG. 3, and the single crystal parameters are shown in Table 3.

TABLE 3 the single crystal parameters of compound 3

| | |
|---|---|
| Molecular formula | $C_{55}H_{99}CaMn_4NO_{24}$ |
| Molecular weight (g/mol) | 1466.23 |
| Temperature (K) | 173.15 |
| Wavelength (Å) | 0.71073 |
| Crystal system | Trigonal |
| Space group | R-3 |
| Cell parameter | a = 38.379(4)(Å) |
| | b = 38.379(5)(Å) |
| | c = 35.682(4)(Å) |
| | α = 90.00(°) |
| | β = 90.00(°) |
| | γ = 120.00(°) |
| Volume V(Å$^3$) | 45517(12) |
| Number of molecules in one unit cell | 18 |
| Calculated density Dc(g/cm$^3$) | 0.963 |
| Absorption coefficient (mm$^{-1}$) | 0.590 |
| Single crystal size | 0.79 × 0.27 × 0.25 mm |
| F(000) | 13896 |
| θ range | 0.837-25.200°. |
| Collected data number | 123798 |
| Independent data number | 18194 [R(int) = 0.0512] |
| Final R factor [I > 2σ(I)] | $R_1$ = 0.1345 |
| | $wR_2$ = 0.3763 |
| R factor of all data | $R_1$ = 0.1394 |
| | $wR_2$ = 0.3818 |
| Maximum and minimum electron diffraction densities | 2.832 and −0.923e.Å$^{-3}$ |

Advantageous Effect of the Present Invention

The inventors have found that by using simple $Mn^{+2}$, $Ca^{2+}$ inorganic compounds and simple carboxylic acid, and using permanganate anion as oxidant, asymmetric cluster containing the core of [$Mn_4CaO_4$] can be synthesized in a two-step synthesis. This type of compounds can catalyze the splitting of water on the surface of an electrode or in the presence of an oxidant to releases oxygen, electrons and protons.

The neutral [$Mn_4CaO_4$]($R_1CO_2$)$_8L_1L_2L_3$ cluster obtained according to the present invention can be used as water splitting catalyst, which can be used to drive the catalytic splitting of water on the surface of an electrode, or in the presence of an oxidant (which may be a stable oxidant, or a light-induced transient oxidant), to release oxygen, protons and electrons. This new type of [$Mn_4CaO_4$] catalysts has not been reported in the art.

SPECIFIC MODE FOR CARRYING OUT THE INVENTION

The technical solutions according to the present invention will be illustrated by the following specific examples. Those skilled in the art should understand that the examples are not intended to limit the invention. Any improvements and modifications that may be made on the basis of the invention are within the protection scope of the invention.

Example 1: Compound 1 [$Mn_4CaO_4$]($C_5H_9O_2$)$_8$ ($C_5H_9O_2H$)$_2$($C_5H_5N$)

The preparation process was as follows:

The first step was the synthesis of the precursor of compound 1. To a 100 ml round bottom flask were added tetrabutylammonium permanganate ($Bu^n{}_4NMnO_4$, 4 mmol), manganese acetate ($Mn(CH_3CO_2)_2$, 1 mmol), calcium acetate ($Ca(CH_3CO_2)_2$, 1 mmol) and pivalic acid (($CH_3$)$_3CCO_2H$, 40 mmol). After continuous reaction in acetonitrile at 80° C. for 25 min, the reaction was stopped. The resultant was filtered to remove a small amount of precipitate. The resulting brown mother liquor was allowed to stand at 0° C. for 1-2 weeks to precipitate brown crystals.

The second step was recrystallization. The crystals obtained in the first step were collected and dissolved with ethyl acetate. 2% (volume ratio) pyridine was added for recrystallization. After 1-2 weeks, brown crystals were precipitated, leached with cyclohexane and vacuum dried. The yield was about 40% (according to the mole numbers of Ca ions).

Compound 1 has a structural formula of [$Mn_4CaO_4$ ($R_1CO_2$)$_8$]($L_1$)($L_2$)($L_3$), wherein $R_1$=tert-butyl; $L_1$=pyridine; $L_2$=$L_3$=pivalic acid.

That is, compound 1 has the structural formula of [$Mn_4CaO_4$]($C_5H_9O_2$)$_8$($C_5H_9O_2H$)$_2$($C_5H_5N$).$C_6H_{12}$ (note: the cyclohexane is a solvent molecule) with the molecular formula of $C_{61}H_{109}NO_{24}CaMn_4$. Theoretical values of elemental analysis: C, 48.83; H, 7.32; N, 0.93; experimental values: C, 49.14; H, 7.59; N, 1.18. Compound 1 has a single crystal of monoclinic system, with space group of $P2_1/c1$, cell parameter of a=29.317(7)Å, b=18.894(4)Å, c=29.903(7)Å, α=90.00°, β=104.609(4)°, γ=90.00°, Z=8, and volume of 16028(7)Å$^3$.

Figure 1:
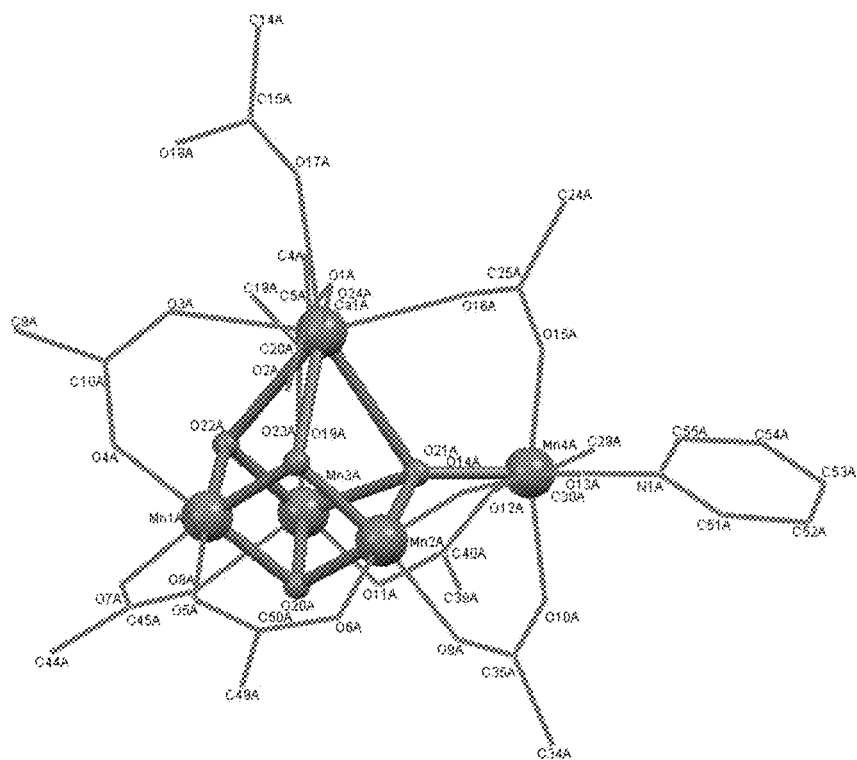
FIG. 1 is the crystal structure diagram of compound 1 prepared in Example 1 of the present invention. For the sake of clarity, the hydrogen atom, the methyl of tert-butyl and solvent molecules are all omitted.

Compound 1 has the chemical structure shown by the Formula I-1 below, the determined specific single crystal parameters shown in Table 1, and the crystal space structure shown in FIG. 1.

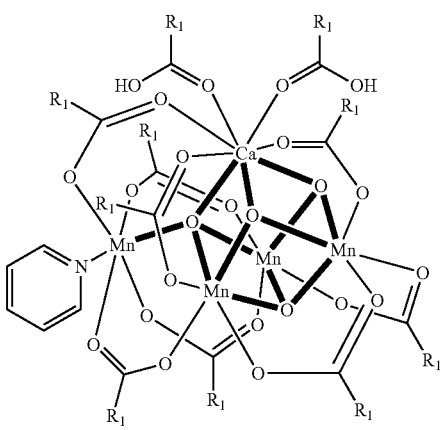

Formula I-1 wherein $R_1$ is tert-butyl

Example 2: Compound 2 [Mn$_4$CaO$_4$](C$_5$H$_9$O$_2$)$_8$(C$_5$H$_9$O$_2$H)$_1$(C$_5$H$_5$N)$_2$ 0.100 g compound 1 was weighed and dissolved in ethyl acetate, to which 1% pyridine was added, and the mixture was allowed to stand at room temperature for 3 weeks to precipitate black crystals, which was then leached with cyclohexane and vacuum dried. The yield was about 13% (according to the mole numbers of Ca ions).

Compound 2 has a structural formula [Mn$_4$CaO$_4$(R$_1$CO$_2$)$_8$](L$_1$)(L$_2$)(L$_3$), wherein R$_1$=tert-butyl; L$_1$=L$_2$=pyridine; L$_3$=pivalic acid.

That is, compound 2 has the structural formula of [Mn$_4$CaO$_4$](C$_5$H$_9$O$_2$)$_8$(C$_5$H$_9$O$_2$H)$_1$(C$_5$H$_5$N)$_2$ with the molecular formula of C$_{55}$H$_{92}$N$_2$O$_{22}$CaMn$_4$. Theoretical values of elemental analysis: C, 47.42; H, 6.66; N, 2.01; experimental values: C, 47.74; H, 6.89; N, 1.69.

Figure 2:
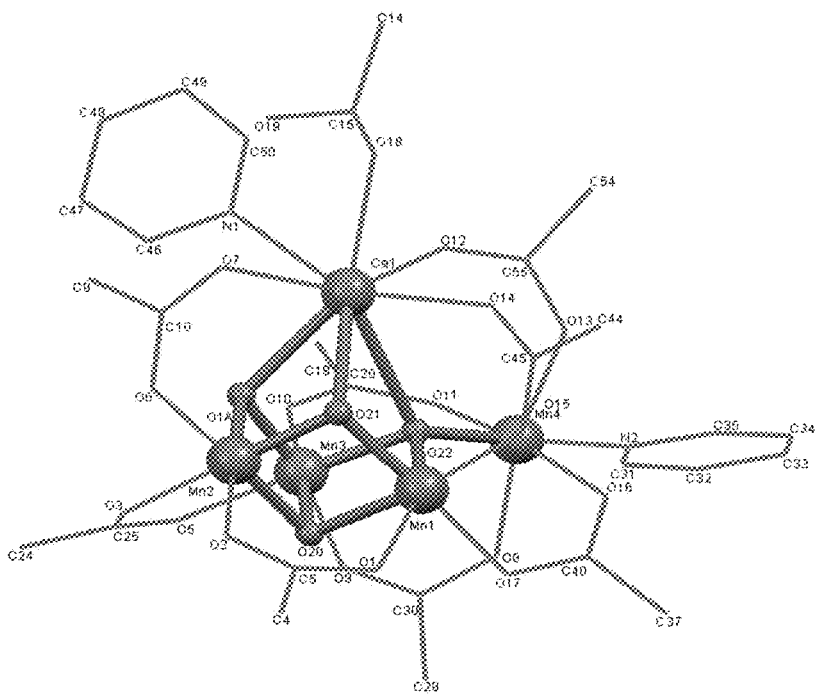
FIG. 2 is the crystal structure diagram of compound 2 prepared in Example 2 of the present invention. For the sake of clarity, the hydrogen atom, the methyl of tert-butyl and solvent molecules are all omitted.

Compound 2 has a single crystal of monoclinic system, with space group of P2$_1$/c1, cell parameter of a=21.969(4)Å, b=25.326(5)Å, c=29.236(6)Å, α=90.00°, β=102.70(3)°, γ=90.00°, Z=8, and volume of 15869(6)Å$^3$. Compound 2 has the chemical structure shown by the Formula I-2 below, the determined specific single crystal parameters shown in Table 2, and the crystal space structure shown in FIG. 2.

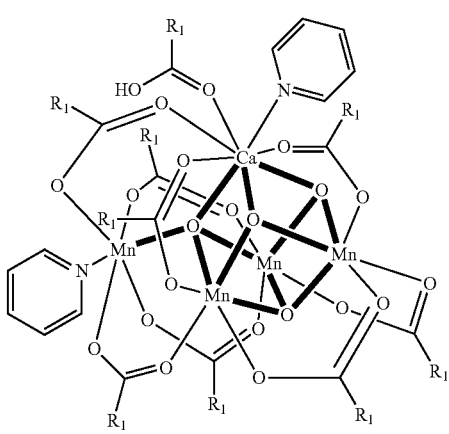

Formula I-2 wherein $R_1$ is tert-butyl

Example 3: Compound 3 [Mn$_4$CaO$_4$](C$_5$H$_9$O$_2$)$_9$(C$_5$H$_9$O$_2$H)$_2$(C$_9$H$_7$N)

The first step was the synthesis of compound precursor. To a 100 ml round bottom flask were added tetrabutylammonium permanganate (Bu$^n$$_4$NMnO$_4$, 4 mmol), manganese acetate (Mn(CH$_3$CO$_2$)$_2$, 1 mmol), calcium acetate (Ca(CH$_3$CO$_2$)$_2$, 1 mmol) and pivalic acid ((CH$_3$)$_3$CCO$_2$H, 40 mmol). After continuous reaction in acetonitrile at 80° C. for 25 min, the reaction was stopped. The resultant was filtrated to remove a small amount of precipitate. The resulting brown mother liquor was allowed to stand at 0° C. for 1-2 weeks to precipitate brown crystals.

The second step was recrystallization. The crystals obtained in the first step were collected and dissolved with ethyl acetate, to which 1% (volume ratio) isoquinoline was added for recrystallization. After 1-2 weeks, black crystals were collected, leached with cyclohexane and vacuum dried. The yield was about 40% (according to the mole numbers of Ca ions).

Compound 3 has a structural formula of [Mn$_4$CaO$_4$(R$_1$CO$_2$)$_8$](L$_1$)(L$_2$)(L$_3$), wherein R$_1$=tert-butyl; L$_1$=isoquinoline, L$_2$=L$_3$=pivalic acid.

That is, compound 3 has the structural formula of [Mn$_4$CaO$_4$](C$_5$H$_9$O$_2$)$_9$(C$_5$H$_9$O$_2$H)$_2$(C$_9$H$_7$N) with the molecular formula of C$_{59}$H$_{99}$NO$_{24}$CaMn$_4$. In the elemental analysis of compound 3, theoretical values are: C, 48.33; H, 6.81; N, 0.96, and experimental values are C, 48.21; H, 6.81; N, 1.06. Compound 3 has a single crystal of trigonal system, with space group of R-3, cell parameter of a=38.379(5)Å, b=38.379(5)Å, c=35.682(7)Å, α=90.00°, β=90.00°, γ=120.00°, Z=18, and volume of 45517(12)Å$^3$.

Figure 3:
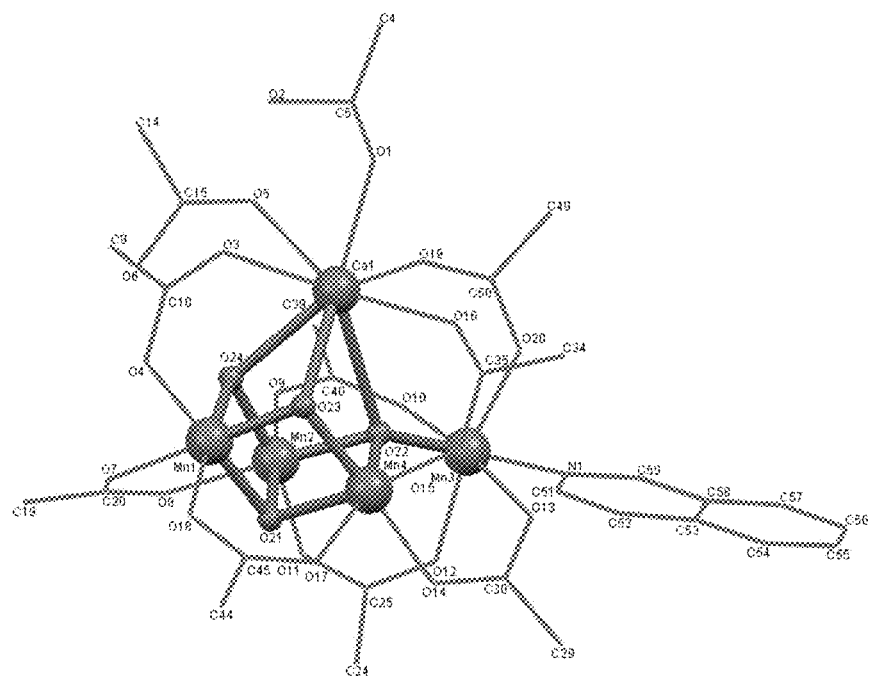
FIG. 3 is the crystal structure diagram of compound 3 prepared in Example 3 of the present invention. For the sake of clarity, the hydrogen atom, the methyl of tert-butyl and solvent molecules are all omitted.

Compound 3 has the chemical structure shown by the Formula I-3 below, the determined specific single crystal parameters shown in Table 3, and the crystal space structure shown in FIG. 3.

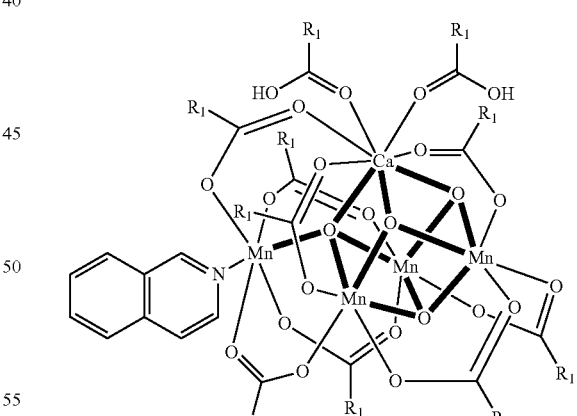

Formula I-3 wherein $R_1$ is tert-butyl

Figure 4:
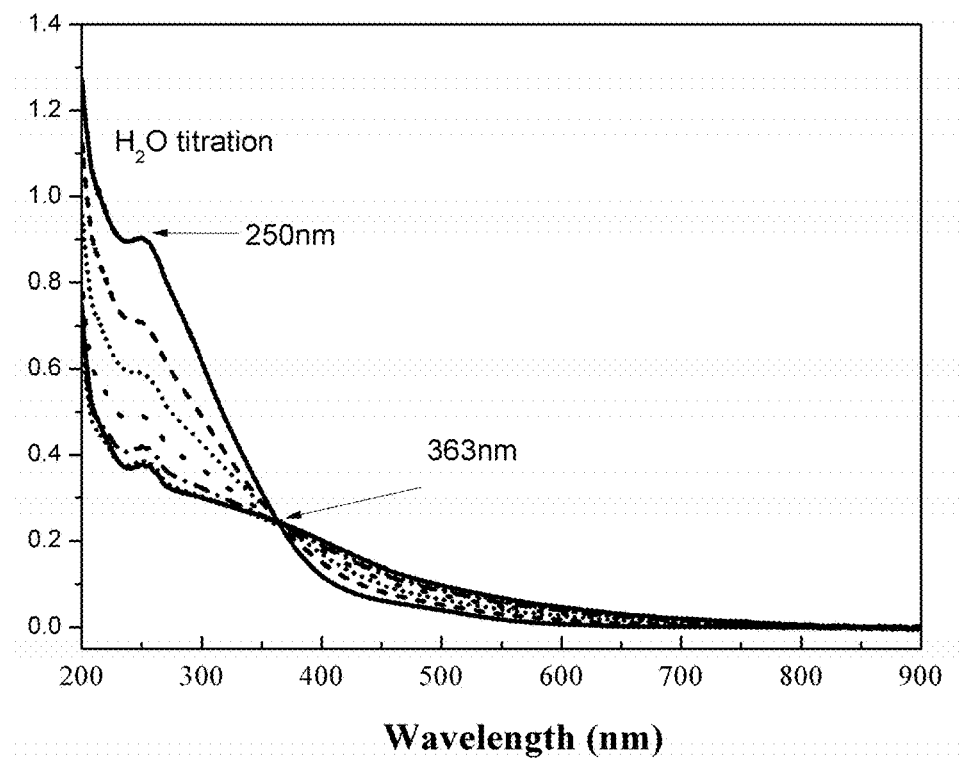
FIG. 4 shows the trace of the change in UV-Vis absorption spectrum of the action between compound 1 and water in Example 4 of the present invention.

Example 4: Trace of the UV-Vis Spectrum of the Action Between Compound 1 and Water To a colorimetric ware was added 1 mL acetonitrile solution of 25 μM compound 1. Using 1 mL pure acetonitrile as reference, absorption spectrum was determined in Hitachi U-3900 spectrophotometer type UV-Vis spectrometer (see FIG. 4). This compound had the maximum absorption at 250 nm. Accompany with the addition of water molecules (0%, 0.2%, 0.4%, 0.6%, 0.8% and 1.0% water being added respectively), the absorption spectrum changed significantly. Specifically, the absorption at 250 nm decreased significantly, while the absorption in the visible region (400-800 nm) increased significantly, and an isobestic point was observed at 363 nm, which indicated that water molecules acted with compound 1.

Figure 5:
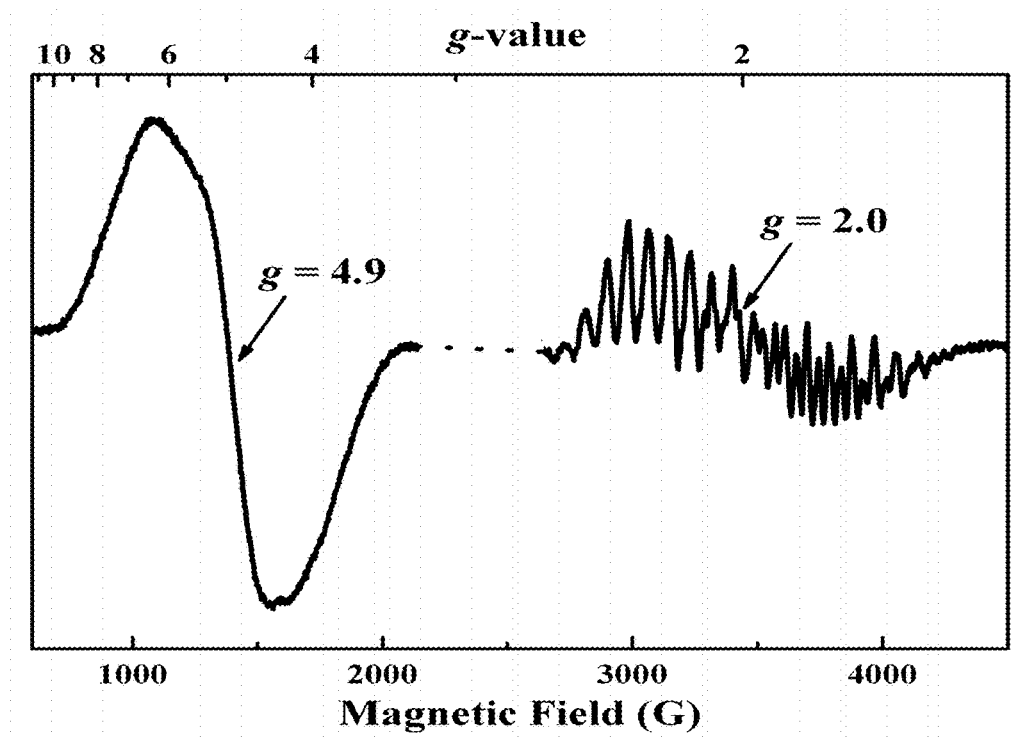
FIG. 5 shows the electrochemical data of compound 1 per se and its catalytic splitting of water on the surface of electrode to release electrons in Example 5 of the present invention.

Example 5: Electron Paramagnetic Resonance of Compound 1 for Detecting the Valence State of Mn Ions in the Compound Compound 1 (1 mM) was dissolved in dichloroethane, and then 0.5 mM oxidant [Fe(Phen)$_3$](PF$_6$)$_3$ was added. The mixture was then rapidly frozen to 77K and its electron paramagnetic signals were detected with Bruker E500 electron paramagnetic resonance instrument at 7K (see FIG. 5). We could clearly see the paramagnetic signals of g=2.0 and g=4.9. The occurrence of these two signals indicated that after the compound was oxidized, the valence states of the four manganese ions were respectively +3, +4, +4 and +4. Thus we could infer that the valence states of the four Mn ions in the ground state (stable state before oxidation) of the compound were +3, +3, +4 and +4 repectively.

Figure 6:
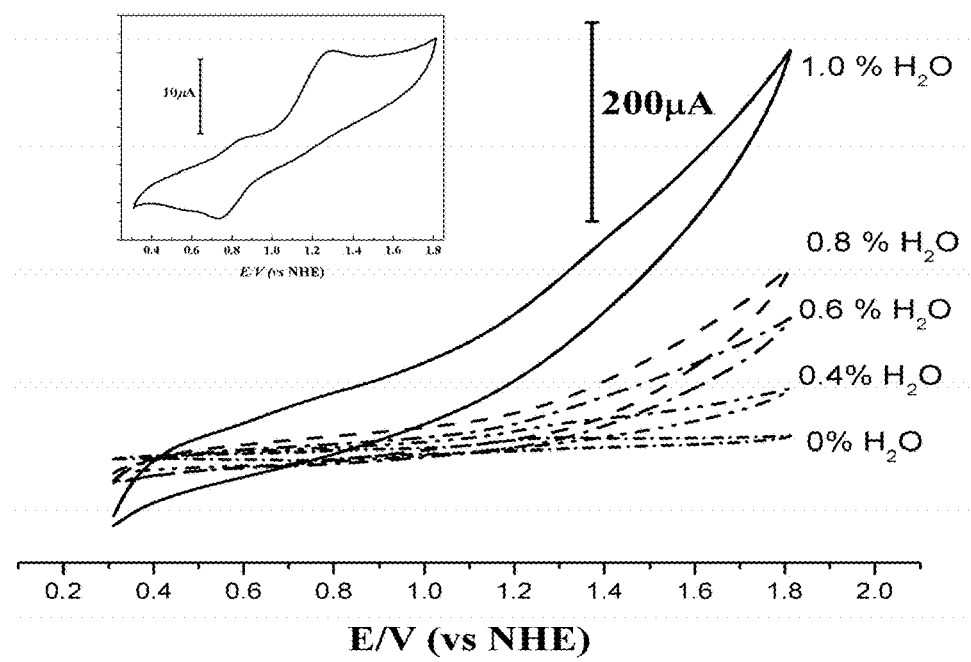
FIG. 6 shows the electron paramagnetic signal given by oxidized compound 1 in Example 6 of the present invention. The data support that the valence states of the four Mn ions in the ground state of compound 1 are +3, +3, +4 and +4 respectively.

Example 6: Electrochemical Determination of Compound 1 and its Catalysis of Water Splitting on the Surface of an Electrode An electrochemical workstation was used to trace the electrochemistry of compound 1 and its catalysis of water splitting on the surface of an electrode. The working electrode was glassy carbon electrode, the counter electrode was platinum electrode, and silver/silver nitrate (10 mM) was the reference electrode. The electrolyte solvent was acetonitrile, the electrolyte was tetrabutylphosphorus hexafluoride (C$_4$H$_9$)$_4$NPF$_6$) and the scanning speed was 100 mV/s. The inset of FIG. 6 showed the cyclic voltammetry curve of compound 1 in the absence of water. Two oxidation processes could be observed with their corresponding potentials of 0.8 V and 1.32 V, respectively. Upon the presence of a small amount of water (the corresponding water contents of the curves in the figure were 1%, 0.8%, 0.6%, 0.4% and 0% successively), the two oxidation couple became not clear. Instead, a rapidly increasing process, corresponding to the water splitting process, was observed. As can be seen from the figure, when 1% water was present, the current value generated by the electrons released by water splitting could exceed 400 µA. This indicated that compound 1 could catalyze the splitting of water very effectively on the surface of the electrode and transfer the released electrons onto the surface of the electrode to form a current.

Figure 7:
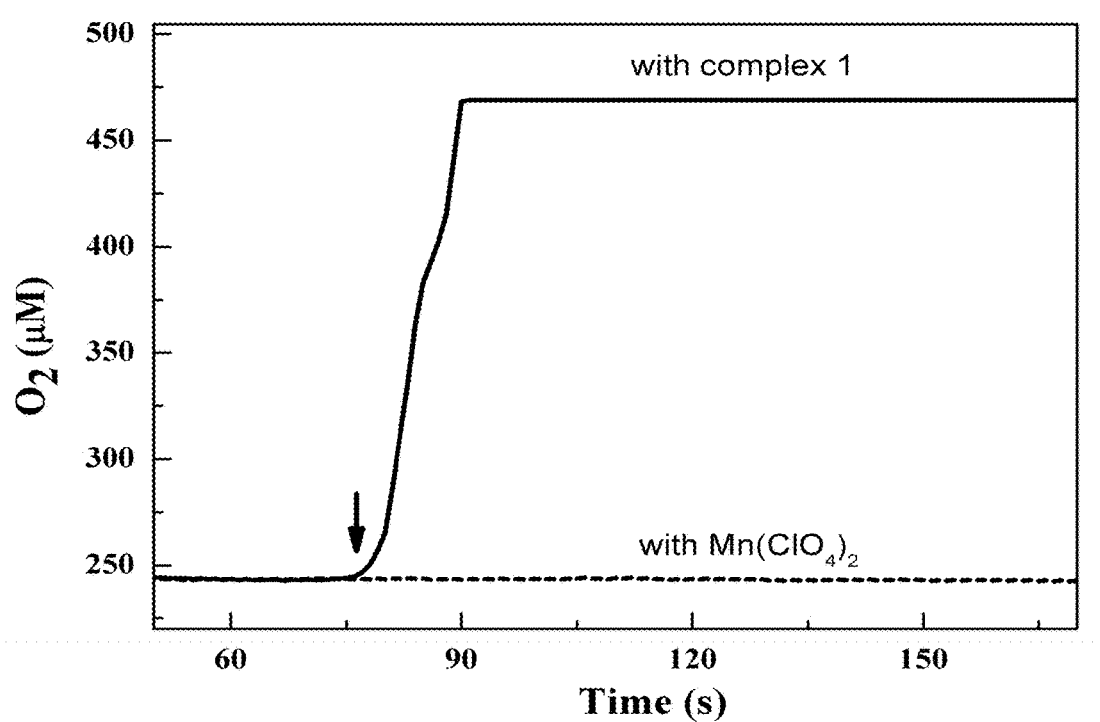
FIG. 7 shows the determination of the oxygen released by the water splitting catalyzed by the compound 1 in the presence of oxidant in Example 7 of the present invention.

Experimental Example 7: Determination of the Oxygen Released by the Water Splitting Catalyzed by the Compound 1 in the Presence of Oxidant The activity for releasing oxygen by the catalysis of water splitting was determined on a Clark-type oxygen electrode (FIG. 7). A rapid release of oxygen can be observed by the addition of 125 µM of compound 1 in an aqueous solution containing an oxidant (tert-butyl hydroperoxide, 0.7 M), while no formation of oxygen could be observed at all with the addition of the reference compound (Mn(ClO$_4$)$_2$). The arrow in the figure showed the loading position of the sample. FIG. 7 indicated that compound 1 had the catalytic activity of catalyzing the splitting of water to release oxygen.

The invention claimed is:

1. A [Mn$_4$CaO$_4$](R$_1$CO$_2$)$_8$(L$_1$)(L$_2$)(L$_3$) compound of Formula I, comprising an asymmetric [Mn$_4$CaO$_4$] heteronuclear metal cluster skeleton core having four Mn ions and one Ca$^{2+}$ ion linked via four O$^{2-}$ ions; and peripheral ligands that are eight carboxylic acid anions and three neutral ligands (L$_1$, L$_2$, L$_3$);

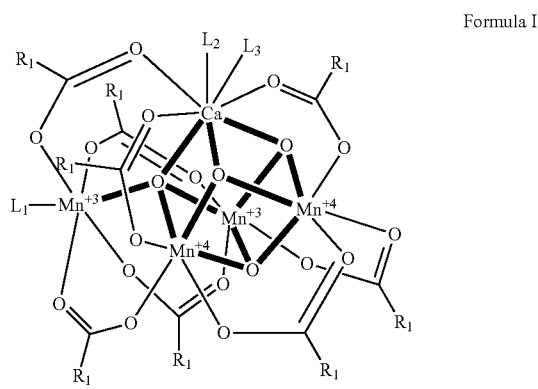

Formula I wherein,

R$_1$ is H or a C$_{1-8}$ linear or branched alkyl;

the three ligands L$_1$, L$_2$, and L$_3$ are the same or different and are each independently selected from the group consisting of carboxylic acid molecules, pyridine, imidazole, pyrazine, quinoline, isoquinoline, H$_2$O, alcohol molecules, ketones, nitriles, and esters, wherein two of the four Mn ions have a valance state of +3 and the other two of the four Mn ions have a valance state of +4.

2. The compound according to claim 1, wherein the compound is electrically neutral.

3. The compound according to claim 1, wherein the carboxylic acid anion (R$_1$CO$_2^-$) is selected from the group consisting of formic acid, acetic acid, propionic acid, butyric acid, isobutyric acid, valeric acid, isovaleric acid, pivalic acid, and hexanoic acid.

4. The compound according to claim 1, wherein the compound is

[Mn$_4$CaO$_4$(R$_1$CO$_2$)$_8$](L$_1$)(L$_2$)(L$_3$), wherein R$_1$=tert-butyl; L$_1$=pyridine; L$_2$=L$_3$=pivalic acid;

[Mn$_4$CaO$_4$(R$_1$CO$_2$)$_8$](L$_1$)(L$_2$)(L$_3$), wherein R$_1$=tert-butyl; L$_1$=L$_2$=pyridine; L$_3$=pivalic acid; or

[Mn$_4$CaO$_4$(R$_1$CO$_2$)$_8$](L$_1$)(L$_2$)(L$_3$), wherein R$_1$=tert-butyl; L$_1$=isoquinoline, L$_2$=L$_3$=pivalic acid.

5. The compound according to claim 4, wherein the compound is

[Mn$_4$CaO$_4$(R$_1$CO$_2$)$_8$](L$_1$)(L$_2$)(L$_3$), wherein R$_1$=tert-butyl; L$_1$=pyridine; L$_2$=L$_3$=pivalic acid; its single crystal being monoclinic, space group being P2$_1$/c1, cell parameter being a=29.317(7)Å, b=18.894(4)Å, c=29.903(7)Å, α=90.00°, β=104.609(4)°, γ=90.00°, Z=8, volume being 16028(7)Å$^3$, and its structure being shown as in Formula I-1:

Formula I-1

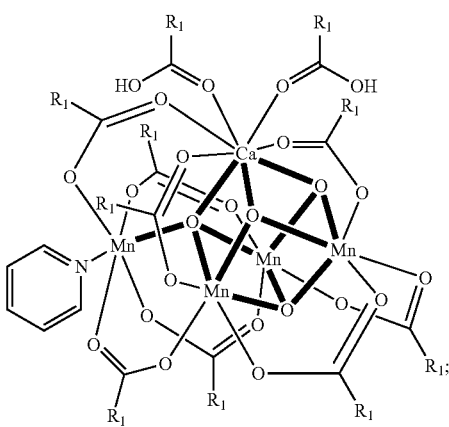

[Mn$_4$CaO$_4$(R$_1$CO$_2$)$_8$](L$_1$)(L$_2$)(L$_3$), wherein R$_1$=tert-butyl; L$_1$=L$_2$=pyridine; L$_3$=pivalic acid; its single crystal being monoclinic, space group being P2$_1$/c1, cell parameter being a=21.969(4)Å, b=25.326(5)Å, c=29.236(6)Å, α=90.00°, β=102.70(3)°, γ=90.00°, Z=8, volume being 15869(6)Å$^3$; and its structure being shown as in Formula I-2:

Formula I-2

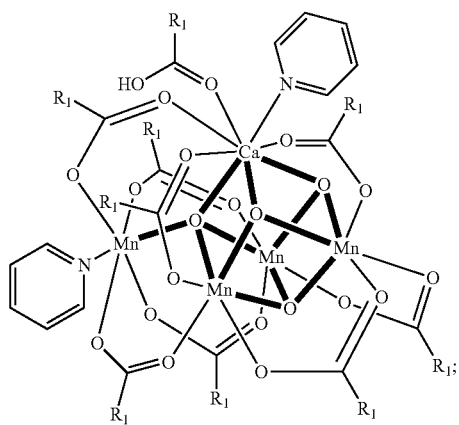

or [Mn$_4$CaO$_4$(R$_1$CO$_2$)$_8$](L$_1$)(L$_2$)(L$_3$), wherein R$_1$=tert-butyl; L$_1$=isoquinoline, L$_2$=L$_3$=pivalic acid; its single crystal being trigonal, space group being R-3, cell parameter being a=38.379(5)Å, b=38.379(5)Å, c=35.682(7)Å, α=90.00°, β=90.00°, γ=120.00°, Z=18, volume being 45517(12)Å$^3$; its structure being shown as in Formula I-3:

Formula I-3

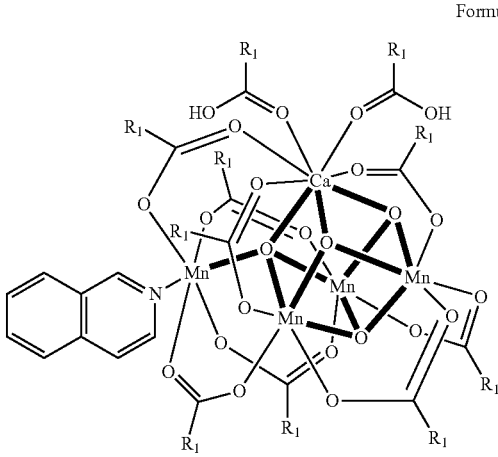

6. A process for preparing the [Mn$_4$CaO$_4$](RCO$_2$)$_8$(L$_1$)(L$_2$)(L$_3$)-compound according to claim 1,

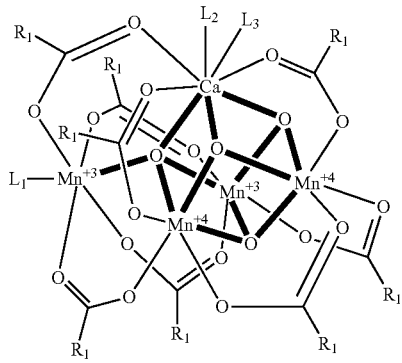

comprising:

step 1: heating a mixture comprising an acid, an oxidant, a Mn$^{2+}$ salt, and a Ca$^{2+}$ salt at a molar ratio of (10-120):(2-8):1:1 in an acetonitrile solvent for 10-60 minutes to obtain a solution, filtering the solution to obtain a filtrate; crystallizing the filtrate at 0° C. to obtain crystals;

step 2: dissolving the crystals obtained from step 1 in an ester solvent, and adding ligands L$_1$, L$_2$ and L$_3$ to the ester solvent to cause recrystallization to obtain the [Mn$_4$CaO$_4$](RCO$_2$)$_8$(L$_1$)(L$_2$)(L$_3$) compound of claim 1.

7. The preparation process according to claim 6, wherein the Mn$^{2+}$ salt is selected from the group consisting of carboxylic acid salts of Mn$^{2+}$; wherein the carboxylic acid anion (R$_1$CO$_2^-$) is formate, acetate, propionate, butyrate, isobutyrate, valerate, isovalerate, pivalate, and hexanoate, Mn(ClO$_4$)$_2$, MnSO$_4$, Mn(NO$_3$)$_2$, Mn(CF$_3$SO$_3$)$_2$, Mn(ClO$_4$)$_2$(H$_2$O)$_n$, MnSO$_4$(H$_2$O)$_n$, Mn(NO$_3$)$_2$(H$_2$O)$_n$, and Mn(CF$_3$SO$_3$)$_2$(H$_2$O)$_n$, wherein n=1-5;

the Ca$^{2+}$ salt is selected from the group consisting of carboxylic acid salts of calcium, wherein the carboxylic acid anion (R$_1$CO$_2^-$) is formate, acetate, propionate, butyrate, isobutyrate, valerate, isovalerate, pivalate, hexanoate Ca(ClO$_4$)$_2$, Ca(NO$_3$)$_2$, Ca(CF$_3$SO$_3$)$_2$, $Ca(ClO_4)_2(H_2O)_n$, $Ca(NO_3)_2(H_2O)_n$, $Ca(CF_3SO_3)_2(H_2O)_n$, wherein n=1-5;

the oxidant is an permanganate anionic oxidant, the acid is acetic acid, propionic acid, butyric acid, isobutyric acid, valeric acid, isovaleric acid, pivalic acid, and hexanoic acid.

8. The preparation process according to claim 7, wherein the oxidant is tetrabutylammonium permanganate (($C_4H_9)_4NMnO_4$).

9. The preparation process according to claim 6, characterized in that a volume of the acetonitrile solvent in step 1 is 60-100 ml acetonitrile per mmol calcium salt;

the ester solvent in step 2 is ethyl acetate, methyl acetate, or propyl propionate.

10. The process according to claim 6, wherein the $[Mn_4CaO_4](R_1CO_2)_8(L_1)(L_2)(L_3)$ compound is electrically neutral.

11. The process according to claim 6, wherein, in the $[Mn_4CaO_4](R_1CO_2)_8(L_1)(L_2)(L_3)$ compound, $R_1$ is hydrogen (H), methyl (—$CH_3$), ethyl (—$C_2H_5$), n-propyl (—$CH_2CH_2CH_3$), isopropyl (—$CH(CH_3)_2$), n-butyl, isobutyl, tert-butyl (—$C(CH_3)_3$), n-pentyl (—$(CH_2)_4CH_3$), or isopentyl (—$CH(CH_3)C_2H_5$).

12. A method to splitting water, comprising:

adding the $[Mn_4CaO_4](R_1CO_2)_8(L_1)(L_2)(L_3)$ compound of claim 1 to water to form a mixture; and adding an oxidant or applying an electric current to the mixture.

13. A water splitting catalyst comprising the $[Mn_4CaO_4](R_1CO_2)_8(L_1)(L_2)(L_3)$ compound according to claim 1.

14. The water splitting catalyst according to claim 13, wherein, the $[Mn_4CaO_4](R_1CO_2)_8(L_1)(L_2)(L_3)$ compound is electrically neutral.

15. The water splitting catalyst according to claim 13, wherein $R_1$ is hydrogen (H), methyl (—$CH_3$), ethyl (—$C_2H_5$), n-propyl (—$CH_2CH_2CH_3$), isopropyl (—$CH(CH_3)_2$), n-butyl, isobutyl, tert-butyl (—$C(CH_3)_3$), n-pentyl (—$(CH_2)_4CH_3$), or isopentyl (—$CH(CH_3)C_2H_5$).

* * * * *